US009119573B2

(12) United States Patent
Lu et al.

(10) Patent No.: US 9,119,573 B2
(45) Date of Patent: *Sep. 1, 2015

(54) STENT MARKER DETECTION USING A LEARNING BASED CLASSIFIER IN MEDICAL IMAGING

(75) Inventors: Xiaoguang Lu, West Windsor, NJ (US);
Terrence Chen, Princeton, NJ (US);
Thomas Pohl, Marloffstein (DE); Peter Durlak, Erlangen (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 1301 days.

This patent is subject to a terminal disclaimer.

(21) Appl. No.: 12/960,635

(22) Filed: Dec. 6, 2010

(65) Prior Publication Data

US 2011/0144480 A1    Jun. 16, 2011

Related U.S. Application Data

(60) Provisional application No. 61/285,228, filed on Dec. 10, 2009.

(51) Int. Cl.
*A61B 6/12* (2006.01)
*A61B 6/00* (2006.01)

(52) U.S. Cl.
CPC . *A61B 6/12* (2013.01); *A61B 6/504* (2013.01); *A61B 6/503* (2013.01)

(58) Field of Classification Search
CPC ........... A61B 6/12; A61B 6/504; A61B 6/503
See application file for complete search history.

(56) References Cited

U.S. PATENT DOCUMENTS

| | | | | |
|---|---|---|---|---|
| 6,904,310 B2* | 6/2005 | Knapp et al. | ................... | 600/431 |
| 7,792,342 B2* | 9/2010 | Barbu et al. | ................... | 382/128 |
| 8,050,482 B2* | 11/2011 | Barbu et al. | ................... | 382/132 |
| 8,311,308 B2* | 11/2012 | Chen et al. | ................... | 382/131 |
| 2012/0004533 A1* | 1/2012 | Peng et al. | ................... | 600/424 |
| 2014/0079308 A1* | 3/2014 | Chen et al. | ................... | 382/132 |
| 2014/0094690 A1* | 4/2014 | Tolkowsky et al. | ........... | 600/424 |
| 2014/0241599 A1* | 8/2014 | Chen et al. | ................... | 382/128 |

OTHER PUBLICATIONS

American Heart Association (AHA), "Heart disease and stroke statistics—2009 update," 2009.
A. Barbu, V. Athitsos, B. Georgescu, S. Boehm, P. Durlak, and D. Comaniciu, "Hierarchical learning of curves application to guidewire localization in fluoroscopy", CVPR 2007.
O. Bertrand, R. De Larochellire, M. Joyal, R. Bonan, R. Mongrain, and J. Tardif, "Incidence of stent under-deployment as a cause of in-stent restenosis in long stents.," International Journal of Cardiovasc Imaging, vol. 20, No. 4, pp. 279-284, 2004.

(Continued)

*Primary Examiner* — Amanda Lauritzen Moher

(57) ABSTRACT

Stent marker detection is automatically performed. Stent markers in fluoroscopic images or other markers in other types of imaging are detected using a machine-learnt classifier. Hierarchal classification may be used, such as detecting individual markers with one classifier and then detecting groups of markers (e.g., a pair) with a joint classifier. The detection may be performed in a single image and without user indication of a location.

11 Claims, 4 Drawing Sheets

(56) References Cited

OTHER PUBLICATIONS

Y. Boykov and M. Jolly, "Interactive graph cuts for optimal boundary and region segmentation of objects in n-d images", ICCV, 2001.
R. A. Close, C. K. Abbey, and J. S. Whiting, "Improved image guidance of coronary stent deployment," Proc. SPIE, vol. 3976, pp. 301-304, Apr. 2000.
W. T. Freeman and E. H. Adelson, "The Design and Use of Steerable Filters", PAMI 1991.
Y. Freund, and R. E. Schapire, "A decision-theoretic generalization of on-line learning and an application to boosting," in European Conference on Computational Learning Theory, 1995.
X. Lu, B. Georgescu, and D. Comaniciu, "Discriminative Joint Context for Automatic Landmark Set Detection from a Single Cardiac MR Long Axis Slice," Proc. FIMH, LNCS 5528, pp. 457-465, Nice, France, Jun. 2009.
J.M. Mishell, K.T. Vakharia, T.A. Portset, Y. Yeghiazarians, and A.D. Michaels, "Determination of Adequate Coronary Stent Expansion Using StentBoost, a Novel Fluoroscopic Image Processing Technique," Catheterization and Cardiovascular Interventions, vol. 69, pp. 84-93, 2007.
J. Ross, D. Langan, R. Manjeshwar, J. Kaufhold, J. Manak, and D. Wilson, "Registration and integration for fluoroscopy device enhancement," Proc. MICCAI, vol. 8, No. 1, pp. 851-858, 2005.
G. Schoonenberg, P. Lelong, R. Florent, O. Wink, and B. Romeny, "The Effect of Automated Marker Detection on in Vivo Volumetric Stent Reconstruction," Proc. MICCAI, LNCS 5242, pp. 87-94, 2008.
U. Sigwart, J. Puel, V. Mirkovitch, F. Joffre, and L. Kappenberger, "Intravascular stents to prevent occlusion and restenosis after transluminal angioplasty," New England Journal of Medicine, vol. 316, pp. 701-706, 1987.

Z. Tu, "Probabilistic Boosting-Tree: Learning Discriminative Models for Classification, Recognition, and Clustering", Proc. International Conference on Computer Vision, pp. 1589-1596, 2005.
P. Viola and M. Jones, "Rapid Object Detection using a Boosted Cascade of Simple Features", IEEE Conf. Computer Vision and Pattern Recognition, 2001.
P. Viola and M. J. Jones, "Robust Real-Time Face Detection," International Journal of Computer Vision, vol. 57, No. 2, pp. 137-154, 2004.
Y. Zheng, A. Barbu, B. Georgescu, M. Scheuering, and D. Comaniciu, "Fast Automatic Heart Chamber Segmentation from 3D CT Data Using Marginal Space Learning and Steerable Features", Proc. International Conference on Computer Vision, 2007.
Y. Zhu, S. Prummer, T. Chen, M. Ostermeier, D. Comaniciu, "Coronary DSA: Enhancing coronary tree visibility through discriminative learning and robust motion estimation", SPIE 2009.
V. Bismuth and R. Vaillant, "Elastic registration for stent enhancement in X-ray image sequences," Proc. International Conference on Image Processing, pp. 2400-2403, 2008.
E. Dubois, S. Sabri, "Noise Reduction in Image Sequences Using Motion-Compensated Temporal Filtering," IEEE Trans. Communications, vol. 32, No. 7, pp. 826-831, 1984.
B. Georgescu, X. Zhou, D. Comaniciu, and A. Gupta, "Database-guided segmentation of anatomical structures with complex appearance," Proc IEEE Conference on Computer Vision and Pattern Recognition, 2005.
I. Kompatsiaris, D. Tzovaras, V. Koutkias, and M. Strintzis, "Deformable Boundary Detection of Stents in Angiographic Images," IEEE Transactions on Medical Imaging, vol. 19, No. 6, pp. 652-662, Jun. 2000.

* cited by examiner

STENT MARKER DETECTION USING A LEARNING BASED CLASSIFIER IN MEDICAL IMAGING

RELATED APPLICATIONS

The present patent document claims the benefit of the filing date under 35 U.S.C. §119(e) of Provisional U.S. Patent Application Ser. No. 61/285,228, filed Dec. 10, 2009, which is hereby incorporated by reference.

BACKGROUND

The present embodiments relate to detecting markers in medical data. In particular, marker detection for medical imaging, such as imaging a cardiac stent, is provided.

Coronary heart disease is the most common cause of death for men and women. To treat narrowing of the artery lumen due to accumulation of atheromatous plaques, a stent is implanted to expand and support the narrowing vessel. A stent is a fine mesh. A guide-wire is first introduced inside the artery. During implantation, the stent is supported by a balloon. The angioplasty balloon equipped with a stent is slid along the guide wire.

Stent deployment is monitored by X-ray fluoroscopy. Proper visualization of the stent, including the stent's location, surrounding tissue and deployed geometry, is important to ensure the quality of stent expansion. Under-deployment of the stent is associated with restenosis and thrombosis. However, some stents have less metal, so are less radiopaque. Drug eluting stents may also be less radiopaque than bare metal stents. Lower X-ray doses may be desired, but result in less image quality. As a result, stent visibility in X-ray images is challenging.

One technique for stent enhancement in X-ray fluoroscopy image sequences is based on motion compensated temporal integration of the stent images. To compensate for heart and/or breathing motion, image frames in an X-ray sequence are registered to align the stent. In order to assess the location of the stent, the angioplasty balloon is equipped with two heavily radiopaque markers. The image frames are aligned based on the highly contrasted balloon markers. Temporal averaging of all aligned images may allow preserving stent contrast in the image while blurring the background and suppressing noise, leading to improved stent visibility. While the moving background in the registered image sequence is blurred, the stent is preserved.

The markers may be detected in the images using match filters. A template of expected intensity response of the markers is correlated with the image. The highest correlation indicates the location of the markers. Markers may alternatively be detected using blob detection with automatic scale selection. Uniform intensity distribution within a shape is identified. This "blob" information is searched for in data at different scales. However, these marker detection techniques may have limited capability to cope with large variations and cluttered background presented in real applications. For instance, some patients have had previous interventions, such as open-heart surgery or stent placement. The placed sternal wires, stitches, stents, and other devices in such patients introduce locally similar structures to the balloon markers. Such similar structures may result in detection of a significant number of false markers. Large variations of marker appearance across time may also make it difficult for conventional detection algorithms to consistently differentiate balloon markers, especially when the target markers are overlaid with other structures in the image. Conventional balloon marker detection may depend upon temporal coherence to compensate detection errors among individual image frames and may require user interactions to achieve desired performance.

BRIEF SUMMARY

By way of introduction, the preferred embodiments described below include methods, computer readable media, and systems for marker detection. Stent markers in fluoroscopic images or other markers in other types of imaging are detected using a machine-learnt classifier. Hierarchal classification may be used, such as detecting individual markers with one classifier and then detecting groups of markers (e.g., a pair) with a joint classifier. Cascaded classification may be used. The detection may be performed without user indication of a location.

In a first aspect, a method is provided for marker detection in fluoroscopic imaging of a stent. A plurality of possible markers for a stent is individually detected in one frame of fluoroscopic data without information from other frames of fluoroscopic data. The individual detecting is with a first machine-trained classifier. A pair of markers is jointly detected from the plurality of possible markers for the stent output from the individually detecting. The joint detecting is with a second machine-trained classifier. An image representing information about the pair of markers is output.

In a second aspect, a non-transitory computer readable storage medium has stored therein data representing instructions executable by a programmed processor for marker detection in medical imaging. The storage medium includes instructions for: applying a machine learning-based marker detection to a fluoroscopy image, and outputting a first location of a marker in the fluoroscopy image, the first location determined as a function of the machine learning-based marker detection.

In a third aspect, a system is provided for marker detection in medical imaging. A memory is operable to store data representing a vessel with at least two markers for a stent. A processor is configured to detect, the at least two markers from the data by first detecting possible markers separately and then second detecting the at least two markers jointly from combinations of the possible markers. A display is operable to display an image of the at least two markers.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Coronary artery disease may be treated with deployment of a stent, which is monitored by X-ray fluoroscopy. It is a common approach to use balloon markers to facilitate stent enhancement in the x-ray images. A learning-based algorithm automatically detects balloon markers separately or independently in each image. A probabilistic boosting tree may learn discriminative models based on contextual features that are automatically selected through learning process. Learning-based methods may handle large image variations by exploring context around the target. In addition to context of each individual marker, joint context constructed by pair or other group of markers encodes local shape and appearance. A combination of individual marker and joint marker pair detections may effectively distinguish the target markers from other structures in the image.

Balloon marker detection accuracy from a single image frame is performed in a fully automatic fashion. Temporal coherence based techniques, such as using distance consistency constraint between a pair of markers over time, may still be applied to further improve marker detection across frames in a sequence. Following marker detection, temporal coherence and motion compensation techniques may use marker detection from multiple images. Marker detection in other types of images and/or for other structures may be used.

The marker detection may be used for stent enhancement. For example, the markers are used to align images of a stent. The aligned images are combined to maintain or enhance stent information while reducing or blurring background information. Marker detection may be used for other purposes, such as to measure a distance. In one embodiment, the marker detection herein is used for the imaging methods, computer readable media, and systems disclosed in U.S. Published Application No. 20110142318, the disclosure of which is incorporated herein by reference.

Figure 1:
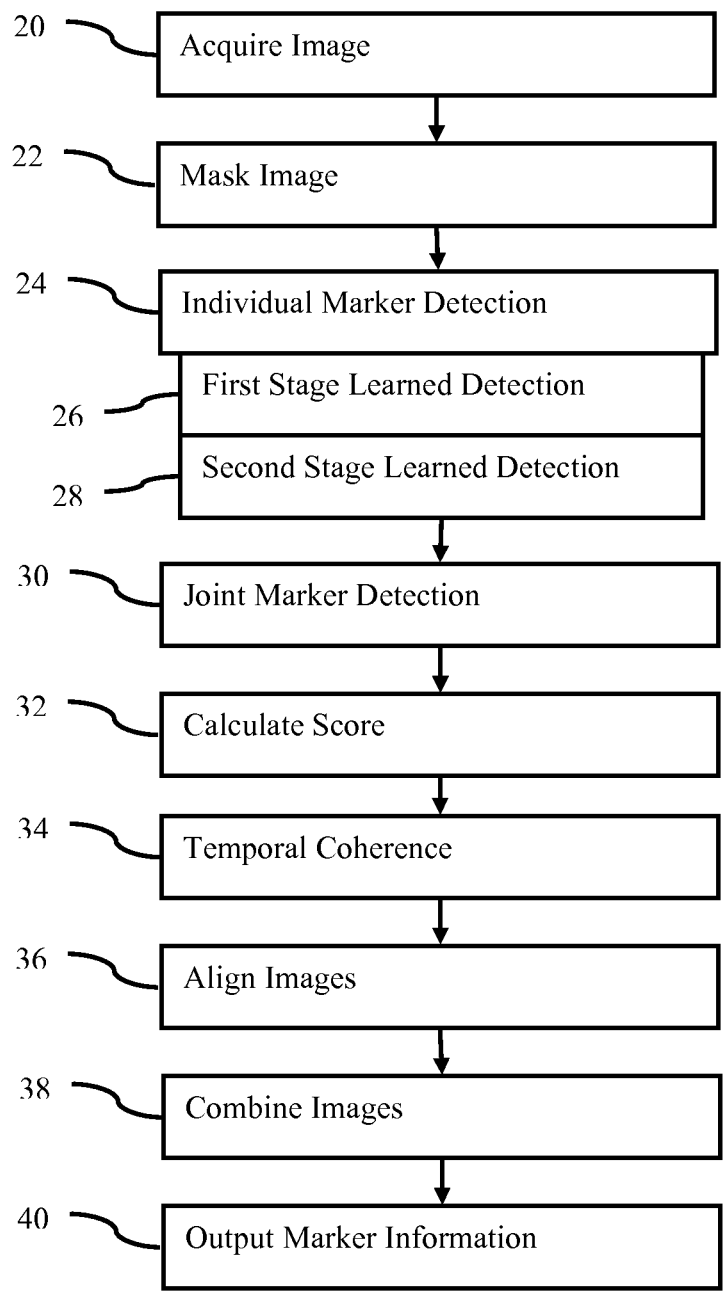
FIG. 1 is a flow chart diagram of an embodiment of a method for marker detection in medical imaging.

FIG. 1 shows a method for marker detection in fluoroscopic or other imaging of a stent or other marked object. The method is implemented by a medical diagnostic imaging system (e.g., a fluoroscopy system), a review station, a workstation, a computer, a PACS station, a server, combinations thereof, or other device for image processing medical data. For example, the system or computer readable media shown in FIG. 6 implements the method, but other systems may be used.

Additional, different, or fewer acts may be performed. For example, acts 24 and 30 are provided without other acts. As another example, act 28 is not provided. In another example, acts 34, 36, 38, and/or 40 are not provided.

The method is implemented in the order shown or a different order. For example, the images are masked in act 22 prior to acquiring the images for marker detection in act 20. The acts are performed in real-time, such as during scanning of the patient. The user may view images of act 40 while scanning to acquire additional images. Alternatively, the images are associated with previously acquired scanning or are provided after scanning.

In one embodiment, automatic detection of balloon markers is provided. The markers for the balloon are for placement of the stent, but may be positioned on other stent related structure. The balloon for expanding the stent may have one or more (e.g., a pair on each end of the balloon or near the ends of the stent) markers for the stent, such as a pair of markers with one on each end of the stent. The guide wire or other structure associated with the stent may have one or more markers for the stent. Markers may be provided in any combination on one or more of these stent related structures. The markers are radiopaque in order to be viewed in x-ray images. By detecting the markers associated with the stent, such as on the balloon, markers for the stent are detected.

In act 20, medical images are acquired. The medical images are displayed information or information for display. Information for display may be red, green, blue (RGB) type display values or may be scalar values prior to mapping for display. For example, the images are scalar values organized as frames of data. Each frame of data corresponds to a scan of a region. The frame of data is data that has been or has not yet been used to display an image. Image may be used to refer to data before or data used after actual display of an image based on the data.

An input sequence of any number (e.g., >30) of images is acquired, such as 30-50 fluoroscopic images. The images represent a region of the patient, such as a region including a stent, guide wire, and/or contrast agent. For example, the images include two balloon markers indicating the position of a stent. Since the marker detection may be performed on each image independently or on only a single image, a single image is acquired in other embodiments.

In one embodiment, the medical images are fluoroscopy images. Alternatively, x-ray, computed tomography, ultrasound, magnetic resonance, or other types of medical images may be used.

In act 22, the image is masked to limit the number of locations to which marker detection is applied. Limiting the number of locations may speed up the detection. The detector is not applied to the background or masked out locations. Any masking may be used. In alternative embodiments, no masking is used. The marker detection is applied to all locations or a sub-sampling of locations.

In one embodiment, the frame of data is filtered. The filter kernel is selected to highlight or maintain structure associated with likely marker locations. For example, the markers are positioned on or adjacent to a guide wire. By filtering to reduce intensities away from wire-like structures, the locations associated with the guide wire are maintained. Steerable filtering may better allow identification of straight or curved linear structure in an image, distinguishing from the background. Steerable filtering filters the gradients determined from intensities. Locations associated with low gradient magnitude in one direction but high gradient magnitude in another direction are more likely associated with a guide wire.

Figures 2A, 2B:
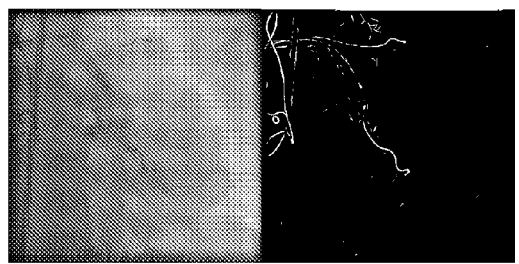
FIGS. 2a and c show example input fluoroscopy images, and FIGS. 2b and d show the example images after masking.
Figures 2C, 2D:
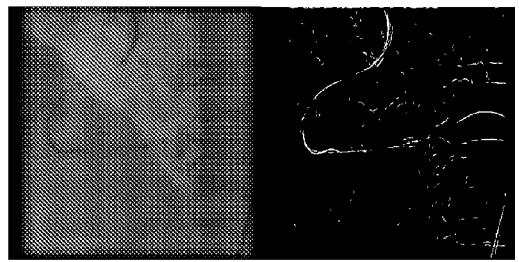

A binary or other criteria identifies the locations of interest from the filtered output. For example, a threshold is applied. Intensities above the threshold are maintained, and intensities below the threshold are set to zero or other background level. FIGS. 2*a* and *c* show two example input images. FIGS. 2*b* and *d* show corresponding masked images, where white indicates locations to which detection will be applied and black indicates background locations to which detection will not be applied.

In acts 24 and 30, a machine learning-based marker detector is applied to the frame of data. For example, a machine learnt classifier is applied to a fluoroscopy image to detect markers. Only one classifier is applied to determine individual markers or groups of markers. Alternatively, a series of classifiers are applied. A hierarchal or cascaded approach may be used, such as detecting possible markers individually and then detecting likely pairs from the detected individual possibilities. The joint context associated with possible pairs of individually detected markers may be used. The individual classifier, joint classifier, or both classifiers use a machine-learnt model or models. FIG. 1 shows an example of the hierarchal approach.

Figure 3:
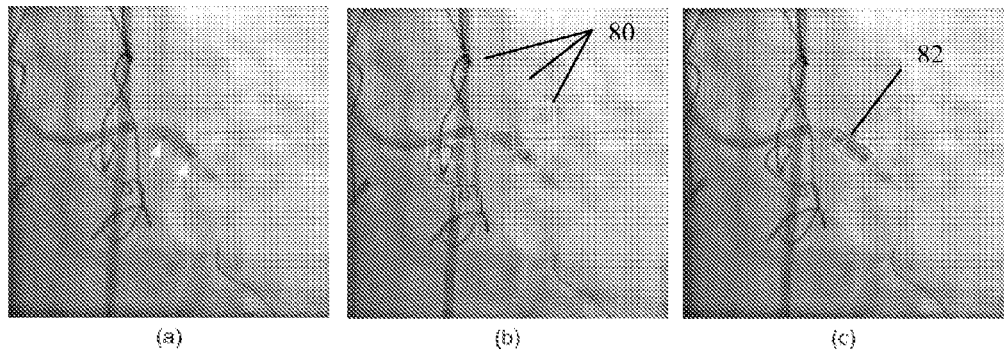
FIGS. 3a-c show medical images for a marker detection sequence in one example.

In act 24, a plurality of possible markers for a stent is individually detected. FIG. 3a includes two arrows showing a pair of balloon markers in a fluoroscope image. Other locations in the image may have similar characteristics, so the marker detector may identify the actual markers and one or more other markers. Since the classifier is not exact or does not identify with 100% accuracy, one or both actual markers may not be identified, only the actual markers may be identified, or combinations of the actual marker and other locations may be identified. The identified locations are possible markers, whether actual markers or not.

The possible markers are detected in one frame of data without information from other frames of data. For example, the balloon markers are detected in a reference frame of data or in each of a plurality of frames of data independently. In alternative embodiments, information from another frame of data is used for individual marker detection in the frame of data.

Each marker is detected without reference to other possible markers. The individual marker detection is independent of other markers. Any number of possible markers may be detected, such as all that satisfy the detection criteria. Alternatively, a limited number of possible markers are detected, such as detecting until the limit is reached or selecting the most likely possible markers.

A first machine-trained classifier individually detects the possible markers. A data-driven, learning-based approach detects balloon markers from single image frames. Marker detection is formulated as an object detection task. Using machine learning, the classifier is trained with target markers (positives) against randomly selected background samples. The classifier quickly removes negatives.

The machine-trained classifier is any one or more classifiers. The classifier may be a model or detector using imaging processing, filtering, or other techniques. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

The classifier is trained from a training data set using a computer. To prepare the set of training samples, actual markers in a number of images are manually annotated. The images are divided into local image patches containing the markers as the positive set of training samples and patches without markers as the negative training set. Any size patches may be used, such as 50×50 pixels. The size of the patches may be determined by optimizing the machine-trained classifier. Any number of expert annotated frames of data is used.

In one embodiment, the machine-trained classifier is a probabilistic boosting tree classifier. The detector is a tree-based structure with which the posterior probabilities of the presence of the marker are calculated from given image data. Each marker detector not only provides a binary decision for a given sample, but also a confidence value (e.g., score) associated with the decision. The nodes in the tree are constructed by a nonlinear combination of simple classifiers using boosting techniques. For example, the classifier has three levels with 40 weak classifiers at each node. The probabilistic boosting tree (PBT) unifies classification, recognition, and clustering into one treatment. Alternatively, a programmed, knowledge based, or other classifier without machine learning is used.

Figure 4:
FIG. 4 shows example filter kernels for Haar wavelet-like features.

For learning-based approaches, the classifier is taught to distinguish based on features. For example, a probability model algorithm selectively combines features into a strong committee of weak learners based on. Haar-like local rectangle filters. Haar features may be rapidly calculated using integral images. FIG. 4 shows example Haar features, where light shading represents positive weights (e.g., +1) and dark shading represents negative weights (e.g, −1). Additional or different features of the same or different type may be used. Features that are relevant to the structure of interest are extracted and learned in a machine algorithm based on the experts' annotations, resulting in a probabilistic model. A large pool of features may be extracted. The large pool is determined by a programmer or may include features systematically determined. The training determines the most determinative features for a given classification and discards lesser or non-determinative features.

The detector is applied to various locations represented by the frame of data. The detector may be applied to all the locations. The frame of data may be decimated by any factor, and the detector applied to the decimated frame of data. In one embodiment, the detector is applied to sample locations likely along a guide wire. The possible or likely guide wire regions are indicated by the mask output in act 22. The detector is applied to the data at each location in the guide wire region or a sub-sampling of such locations.

The context associated with each location is used for detection. For example, the surrounding data for each individual location is used for calculating features, such as a local region for each possible marker in a fluoroscopy image. Not only the possible marker itself, but also the neighboring appearance or context is taken into consideration through a learning-based framework. Context of a marker is considered as its local evidence, such as shape and appearance. Shape and appearance may be separately determined features. In one embodiment, shape and appearance are represented together by Haar wavelet-like features.

Any size may be used for the local region. For example, a 25×25 or 50×50 region is used. A square or other shaped region surrounding a given location may be provided. The marker detection is formulated into an object detection framework to solve a two-class (object vs. background) classification problem. A box (i.e., local region) is used to scan through an image at the guide wire locations to extract candidate samples. Each sample is fed to the learned detector to be assigned a score indicating likelihood of being the target object. From another perspective, marker detection searches the parameter space. For individual markers, the location parameter space has two parameters, x and y. The box based representation is used to include both markers and their context.

FIG. 3b shows detection of possible individual markers in one frame of data using a PBT trained classifier. Marker candidates are individually detected by applying an individual marker detector. The boxes 80 (shown as squares) indicate possible markers and the local context. The whiter or brighter boxes 80 indicate a greater confidence that the detected possible marker is actually a marker. The bluer or darker boxes 80 indicate possible markers with less confidence. As shown in FIG. 3b, the top candidates (i.e., the strongest confidence) may not correspond to the correct markers due to limited discriminative power of individual marker detector in the presence of large inter-class similarities. The boxes 80 define the local regions in which the features are calculated. The boxes reflect the context used for detection, but different context (region sizes) may be used for detection than reflected by the size of the boxes 880.

Where multiple locations in a same region are identified as possible markers, the locations may be consolidated into a fewer number of possible markers. Clustered results are reduced or combined. For example, the context boxes 80 of two or more locations overlap, so are combined into fewer, such as one, possible marker. Any amount of overlap of the boxes, such as by a given percentage or at all, or other distance measure may be used to indicate clustering. The combination of clustered locations is by averaging, such as finding a middle location relative to the locations in the cluster. Other consolidation may be used, such as selecting the location or fewer locations with higher scores.

The output of the individual marker detector applied in act 26 may be used by the joint detector for act 30. Alternatively, the individual marker detection of act 24 includes two stages, acts 26 and 28. Act 26 is performed by application of the machine-trained classifier to identify possible markers from the background as discussed above for act 24. The output of act 26 is applied to yet another classifier, such as another machine-learned classifier, in a cascaded detection structure. The second stage is trained using actual and false markers, such as the possible markers output by the first stage. The machine-trained classifier of the second stage receives the output from the first stage to resolve ambiguities between actual target markers and false similar structures. The second stage is aimed at pruning out more confusing or difficult cases. This two-stage approach results in a more robust and efficient solution. This may reduce false alarms. Some of the possible markers are removed by this bootstrapping strategy.

The machine-trained classifier of the second stage is a same or different type of classifier as for the first stage. For example, a probabilistic boosting tree using Haar features is used for both stages. The first detector is applied to locations along a guide wire to distinguish possible markers from background. The second detector is applied to locations output by the first detector to rule out some of the possible markers as false. Due to the difference in location of application and purpose, the machine learning using the same type of features and type of learning may result in different discriminative features and learned matrices. In alternative embodiments, the second stage classifier is not machine-trained, such as being a knowledge-based program to remove possible markers based on some criteria (e.g., curvature of guide wire through the location).

The second stage detector outputs the same set or a reduced set of possible markers. The output possible markers may include some false markers and may not include one or more actual markers. The output is of the location of the possible marker and a score with or without the context used or box 80.

The first and/or second stage detector may output a score for each of the markers. For example, the second stage may or may not use the confidence from the first stage as an input feature. The second stage may output a different score for a given location. The joint detection may or may not use one or both scores for a given location as a feature. In alternative embodiments, a score is not output by the first stage and/or the second stage.

The score indicates an amount of confidence or probability that a given possible marker is an actual marker. A score is determined for each possible marker output to the joint detector. The score is a probability or a ranking based on the probability but without being an actual probability value (e.g., without being a percentage). For example, the machine trained-classifier outputs a binary score or a score with a greater dynamic range based on the learned information. The higher or lower values indicate the location is more or less likely an actual marker, and the opposite value or values indicate that the location is less likely an actual marker.

FIG. 3b may reflect the output of the first stage or the second stage. In other embodiments, no indication of the score is output. The image of FIG. 3b is shown for understanding and may not be an output image. In other embodiments, such an image is generated.

In act 30, groups of markers are used for joint detection. For example, there may be two actual balloon markers. Different pairs of possible markers are classified together. The possible markers output by the individual detector are used for joint classification. Joint detection detects information for one marker as a function of the other marker. The pair or other group defines the context used for the joint context discriminative model. Every possible combination of possible markers is classified. Alternatively, a limiting criterion is used to select certain combinations of possible markers, such as distance.

To define the joint context for a given group of possible markers, a region around the group is established. For example, a rectangular box is fit over a pair of possible markers. The rectangular box defines the region for which the input feature set is calculated. A machine-trained discriminative joint model provides a flexible scheme to take into consideration joint context constructed by marker pairs or groups. Joint context between a group of markers not only models the geometry but also appearance, resulting in more discriminative features that are not obtainable from individual markers. Adding joint context may significantly resolve large inter-class similarities between true markers and other structures, such as a tip of the guide wire.

The region is defined using any approach. For example, the rectangular box is sized to be 75 pixels wide and just long enough to include the context from all the possible markers included in a given group. As another example, the rectangular box is sized at a specific length-to-width ratio and the length is set to include the individual context from both possible markers in a pair. In yet another example, the boxes 80 and 82 are defined by five parameters, including two positions <x,y>, one orientation <beta>, and two scales <sx, sy>. The parameters for two individual markers are indexed by _a and _b. The parameters for the joint markers are indexed by _j. The location of the context box 82 for the joint detection is calculated based on the locations of the individual markers as: $x\_j=(x\_a+x\_b)/2$; $y\_j=(y\_a+y\_b)/2$. The orientation is calculated as orthogonal to the line segment connecting a and b locations. There may be two possible orientations, where both are valid. The size or scale of the context box 82 for joint detection is calculated as: $sx\_j=\sqrt{((y\_b-y\_a)^2+(x\_b-x\_a)^2)}*1.5$; and $sy\_j=s\_a=s\_b$. FIG. 3c shows an example rectangular box 82 calculated using these equations. Other functions may be used.

For the joint detector, each joint context rectangular box is normalized to a standard box size or scale. The context region for different groups is scaled to a given size. Data may be interpolated to increase scale or decimated to reduce scale. Filtering may or may not be applied. By normalizing the different context regions to a same size, the joint detector may have better performance.

In the pair example for a balloon stent, marker pairs within each image are separately and independently classified. For two marker candidates, $M_a$ and $M_b$, which are represented by their respective parameters θa and θb, the joint context (JC) is defined as a function f(θa, θb). JC is explicitly represented as appearance. JC is contained in the orientated rectangular box that includes both candidate markers along with their neighborhood.

The joint detection is performed with a machine-trained classifier. For example, a probabilistic boosting tree classifier is trained to consider the joint context for a group of possible markers. Other machine-trained classifiers may be used. In other embodiments, the joint classifier is programmed or not machine-trained, such as using a formula or distance information to detect the most likely group of markers as the actual markers.

Any type of features may be used. For example, Haar features are used. The score from the individual marker classifier may be used as an input. In one embodiment, gradient features are used. Computation of gradient features is efficient since image rotation and re-scaling is not needed. Any gradient calculation may be used, such as steerable features. Gradient-based features are extracted at pre-defined sample points in the standardized box 82.

The feature pool may also or only include gradient-derived variants, such as magnitude and angle with respect to certain pre-defined orientations relative to the standardized box 82. The gradient magnitude, a gradient angle, or both are relative to the rectangular box, such as gradients along different angles within the box (e.g., short axis as 0 degrees and long axis as 90 degrees such that the magnitude of gradients at different angles are calculated and/or finding an angle of maximum gradient relative to the box). In one embodiment, the gradient magnitude is calculated after projecting the gradient to pre-defined sample patterns or angles. The absolute value of the magnitude is calculated. The square root of this absolute value is calculated. The absolute value of the magnitude projection to the power of 0.333, 2, and 3 is calculated. The log of the absolute value is calculated. The angle of the gradient, square root of the angle, the angle to the power of 0.333, 2, and 3, and the log of the angle are calculated. Additional, different, or fewer gradient or other features may be determined from the context. Some, none, or all of these features may be selected through machine learning as discriminative.

In one embodiment, the joint detector outputs a score for each of the different groups of possible markers in a given image. The joint detector operates automatically without any user interaction other than to initiate the detection. The pair of markers that have the best detection score from applying the joint detector is identified.

In another embodiment represented by act 32, the scores output by the joint detector are used in combination with scores from one or more individual detectors to select the final group of markers. To select the actual marker group, such as to select the pair of possible markers most likely to indicate the actual markers, the pair with the greatest, least or other identifiable combination score is selected. The combination score is calculated for each combination or group of possible markers.

Any combination may be used for scoring. To integrate evidence obtained from both individual markers and marker pairs or groups, a score fusion is provided at the decision level. For example, the final score (p) of a candidate marker pair is calculated as:

$$p = p(MP \mid I_{<a,b>}) \times \frac{p(M \mid I_a) + p(M \mid I_b)}{2},$$

where M and MP stand for Marker and Marker Pair, respectively, $p(MPII<a,b>)$ is the score from joint context, $I<a,b>$ is constructed by marker candidates a and b, whose context is denoted by Ia and Ib; and $p(MIIa)$ and $p(MIIb)$ represent individual marker detection scores. Other combinations using the same, different, or additional information may be used.

Figure 5:
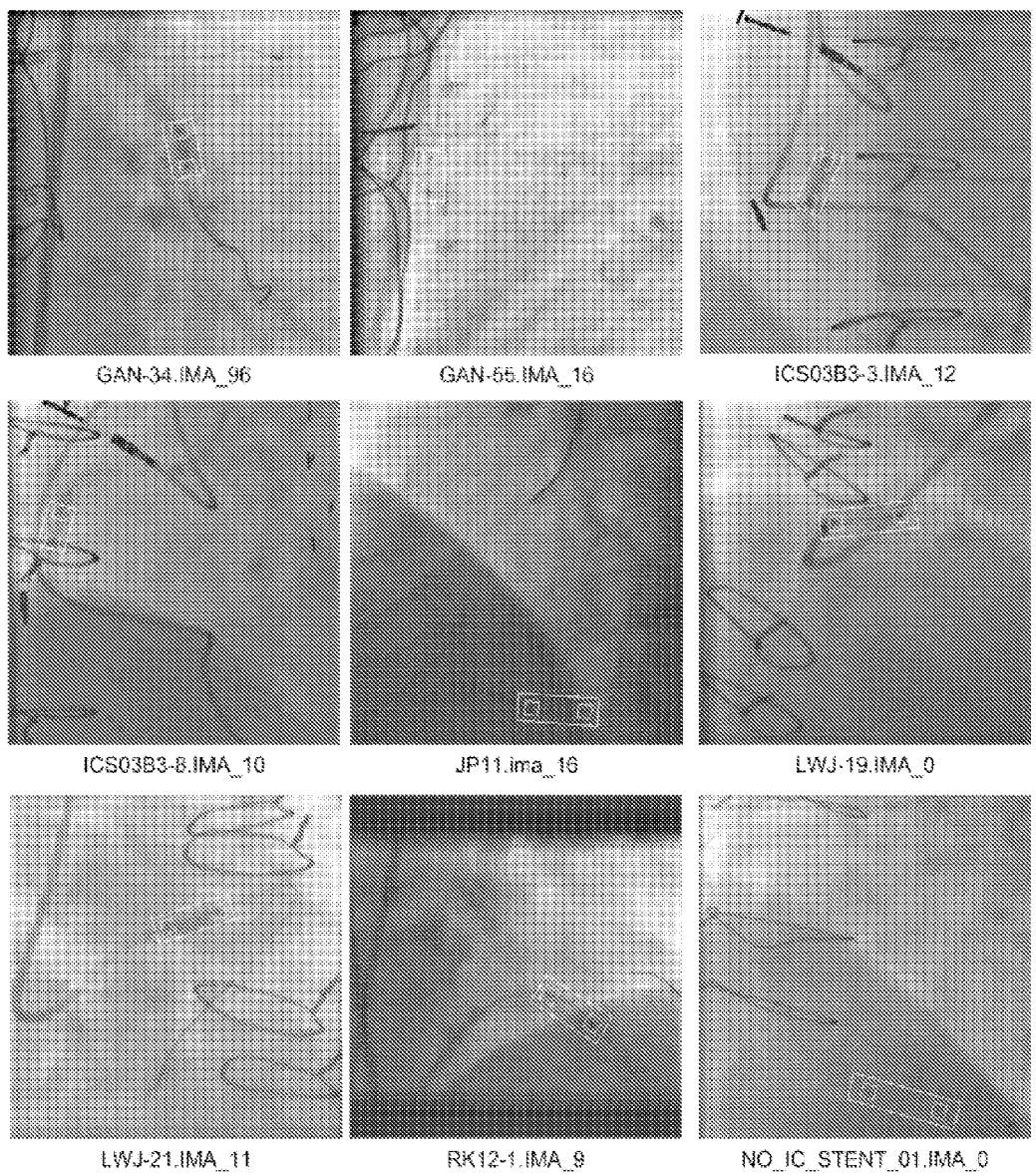
FIG. 5 shows example outputs of marker detection according to one embodiment.

The group (e.g., pair) of markers that have the best combined score is selected as the actual markers. FIG. 3c represents a final detection. The markers are at the center of each square box 80. FIG. 5 shows nine other examples of the final detection.

For a given image, a pair or other group of markers is identified as the actual markers. The process may be repeated for each of a plurality of frames of data. For example, individual and joint detection are repeated for a plurality of frames of fluoroscopic data. Each repetition is performed independently of the detection in other frames.

In optional act 34, temporal coherence is applied to remove outliers or other detected markers that may be inaccurate. The markers of different frames are compared in order to remove markers that may be inaccurately detected. After the detection of the markers in each frame, the detected marker locations in each frame are sorted by their associated detection probability or combination score. Let $M_i^n$ be the detected marker position at frame n. $P(M_i^n)$ is the detection probability. The two markers, $M_1^n$ and $M_2^n$, output from the joint detector are put on the top of the list.

Markers may be removed based on static location. The location of the marker detection may be attracted by the blob-like patterns on the static wire-like structure of the stent or guide wire. Since the ground truth guide wire with the stent is located inside a coronary artery, it is very unlikely that a marker on the guide wire would stay in the same location across different frames. In order to minimize the possibility of such cases, the algorithm scans through all frames and removes locations detected in more than 30% of the frames. If the marker for a given frame is in the same location in more than 30% of the other frames of a sequence, then the markers in the frames with the common locations are removed. Other values than 30% may be used.

A marker reference frame of data is selected from the remaining frames of data. The reference frame is selected based on a distance between markers in the frames of data and the probabilities of the markers in the frames being correct (e.g., scores). The purpose is to identify one frame where the two balloon markers are correctly detected with the highest probability. For example, the combined scores of a joint pair of markers output by the classifier and the distance between the markers of the pair are used. $P_{bm}(i)$ is the probability of the first two balloon markers output from the joint detector being correct. The distance is represented by $d(i, j)=d_1(i, j)+d_2(i, j)$ where $d_1(i, j)=\min(|M_1^i-M_1^j|_{L^2}+|M_2^i-M_2^j|_{L^2}, |M_1^i-M_2^j|_{L^2}+|M_2^i-M_1^j|_{L^2})$ is the sum of distances between the corresponding balloon markers in frame i and j, and $d_2(i, j)=||M_1^i-M_2^i|_{L^2}-|M_1^j-M_2^j|_{L^2}|_{L^1}$ is the difference between the length of the two balloon markers. This distance is a correlation of one frame relative to another in order to indicate the marker frame most like other marker frames. A distance or length value alone may be used. Other functions for distance may be used.

These two variables are used together to select the reference frame. The values for the variables may be normalized and summed. The greatest sum, such as given by:

$$\text{Score}(i) = P_{bm}(i) \times \frac{1}{N-1} \sum_{j, j \neq i} \exp(-d(i, j)^2 / \sigma^2),$$

where N is the total number of frames, j is any frame other than i, and d(i, j) is defined as the distance between frame i and j, is used. Other functions with the same or different variables may be used. The reference frame $r = \text{argmax}_i \text{Score}(i)$ is selected as the reference frame. In alternative embodiments, the probability alone (e.g., pair of markers with the greatest probability) or distance alone is used to select the reference frame.

The reference frame is used to start the process to find the markers in all the other frames. The correct markers are to be identified in the other or remaining frames. The reference frame is used as a starting point in time. Frames from backwards and forwards in time from the reference frame r are examined. The markers identified in the reference frame r are used to check the consistency in frames r+1 and r−1. If the distance d(r, r−1) is smaller than a threshold, the markers in the frame r−1 are added into the list of correct markers. If no balloon marker pairs $(M_a^{r-1}, M_b^{r-1})$ are found in frame r−1, frame r−1 is skipped. The process repeats for other frames, (e.g., r+1, r−2, r+2, r−3 . . . ). The distance function is the one used for selecting the reference frame, but other distance functions may be used. The distance function is a cost function based on the consideration that the markers will not have moved much between frames. The frame with confirmed markers closest in time is used for the distance comparison, but the reference frame may be used for temporally spaced frames in other embodiments. All the frames with consistent marker candidates are output.

Other approaches may be used. For example, temporal coherence is not performed. Instead, the frames with marker pairs with sufficient (e.g., above a threshold) probability are used. As another example, a range of likely motion of the markers is determined and correlated with the heart cycle. If the markers are within expected tolerance given the heart phase or motion, then the markers are considered correct.

Optional acts 36 and 38 are for forming an enhanced image of a stent. By using the detected markers in the individual frames, the stent information in different frames may be aligned. The aligned frames are combined, resulting in enhancement of the stent. The frames used include only frames with markers identified as correct or likely correct. For example, only the frames with temporal coherence output from act 34 are used.

For the stent to be enhanced, the frames of data are aligned in, act 36. Where a pair of markers is used, the markers are aligned. Each of the images with correct markers are rotated, translated, and/or scaled relative to a reference frame or other frame. The rotation, translation, and/or scaling is to position the markers in the same locations. The transform may be rigid or non-rigid. Only rotation and/or translation may be used in other embodiments. Only scaling may be used in other embodiments. In one embodiment, the images are low pass filtered. The filtered images are scaled in a specific orientation. After scaling in the orientation, the scaled images are aligned.

By aligning the markers, the stents are more likely aligned. Since the position of the stent relative to the markers on the balloons or other marker locations is generally consistent, the data representing the stent aligns or is in phase. When the aligned frames are combined, this data sums to a greater level. Other locations likely do not sum to the same extent or are out of phase. For example, heart motion causes the tissue to move. This variance causes the average or sum to be less.

The combination in act 38 is a simple average. Averaging or other combination results in maintaining the stent information while cancelling out more random background information. A sum without normalization may be used. A weighted average may be used, such as with weights that more strongly weight frames associated with a higher probability of correct marker identification. The aligned and compounded frames of data form a stent frame of data or stent image. The stent is enhanced relative to the background in a fluoroscopic or other image.

In act 40, an image representing the markers in one or more frames of data is output. The image is of just the markers, marker information (location, orientation or other), or highlights in a medical image. For example, FIG. 3c shows a fluoroscopic image with a pair of markers highlighted by display of the boxes 80 and 82. Other highlighting may be provided, such as displaying the points or regions of the actual marker in color or with a graphic overlay other than the box (e.g., an asterisk). In alternative or additional embodiments, the image is a stent enhanced image based on the stent frame of data output from act 38. The markers may be enhanced by the combination without further highlighting or further highlighting may be provided.

For displaying the marker information on a medical image, the frame of data representing the patient is mapped to gray scale or color values. In alternative embodiments, the stent or marker region is enhanced by segmentation. FIG. 5 shows example frames of data without stent enhancement but with the markers highlighted by context boxes.

The markers may be detected based on an input sequence of images without user indication of any location in the images. A user seed location, such as to indicate the stent, vessel, vessel wall, center line, guide wire, or segment, is not provided. The user may input settings for the process, such as tolerances or weights, but the process identifies the markers free of locational input. The user activates the process, but does not assist the process in detection.

Figure 6:
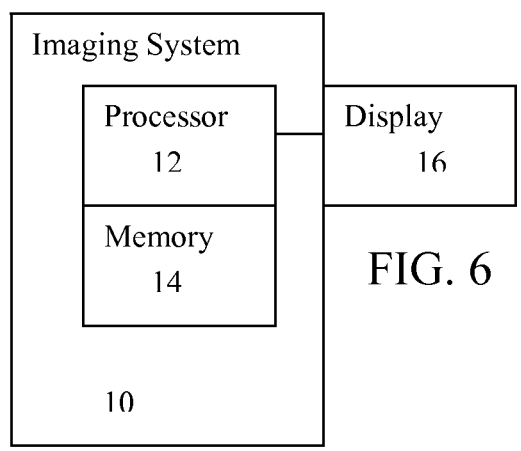
FIG. 6 is a block diagram of one embodiment of a system for marker detection in medical imaging.

FIG. 6 shows a medical diagnostic imaging system 10 for marker detection in medical imaging. The system 10 is a medical fluoroscopy imaging system, but may be a computer, workstation, database, server, or other system. The system 10 includes a processor 12, a memory 14, and a display 16. Additional, different, or fewer components may be provided. For example, the system 10 includes an x-ray source and detector.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10, such as a database or PACS memory.

The memory 14 stores medical imaging data. For example, a fluoroscopy sequence of images is stored. The sequence is acquired over seconds or minutes. The medical imaging data may be a single image. The medical images are of a region including a vessel, a stent, and/or markers (e.g., a pair of markers on a balloon for the stent). The stent may be introduced during acquisition of the sequence or may already be in place during the acquisition. The vessel may or may not include a guide wire for placement of the stent. The data includes a representation of two or more markers for the stent. Other types of medical images may be stored. Alternatively, the medical image data is transferred to the processor 12 from another device with or without storage in the memory 14.

For real-time imaging, the medical data bypasses the memory 14, is temporarily stored in the memory 14, or is loaded from the memory 14. Real-time imaging may allow delay of a fraction of seconds, or even seconds, between acquisition of data and imaging. For example, real-time imaging is provided by generating images of the sequence substantially simultaneously with the acquisition of the data by scanning. To allow better visualization of the stent, especially stents with less metal or radio opaque materials, an enhanced stent image may be generated. In alternative embodiments, the image data is stored in the memory 14 from a previous imaging session and used for detecting markers and/or generating stent enhanced images.

The memory 14 is additionally or alternatively a non-transitory computer readable storage medium with processing instructions. The memory 14 stores data representing instructions executable by the programmed processor 12 for marker detection in medical imaging in medical imaging of a stent. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, graphics processing unit, application specific integrated circuit, field programmable gate array, digital circuit, analog circuit, combinations thereof, or other now known device for processing frames of data for medical images. The processor 12 is a single device, a plurality of devices, or a network. For more than one device, parallel or sequential division of processing may be used. Different devices making up the processor 12 may perform different functions, such as a marker detector and a separate device for generating a stent enhanced image. In one embodiment, the processor 12 is a control processor or other processor of a medical diagnostic imaging system, such as a fluoroscopy imaging system processor. The processor 12 operates pursuant to stored instructions to perform various acts described herein, such as detecting markers in one, two, three, or more stages and/or applying a machine-trained classifier.

The processor 12 performs machine learning and/or applies a machine-learnt algorithm. For example, the processor 12 applies a probabilistic model to detect markers. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. In one embodiment, a PBT classifier is used. The classifier is instructions, a matrix, a learned code, or other software and/or hardware for distinguishing between information in a medical image.

The classifier may include a plurality of models or classifiers (e.g., detectors) operable together or independently. For example, different probabilistic models are trained for different processes, such as a cascade of two or more detectors for individual detection of markers from background and from false positives. The probabilistic models may be joint or dependent.

The different classifiers are the same or different types of classifiers. The same or different types of classifiers may be used for the same type of classification.

In one embodiment, the probabilistic model is formed from a probabilistic boosting tree Classifier. For example, the classifiers are trained using Haar wavelet features, steerable features, other features, calculations there from, or combinations thereof. Any number of features may be used, such as tens, hundreds, or thousands.

For application, the processor 12 calculates features for classification. The features may be for sub-sets of the frames, such as for a plurality of image patches centered on locations. The processor 12 may apply other processes, such as aligning or other acts using the output of the machine-learnt classifiers or not using such output.

The processor 12 is configured to perform any or all of the acts of FIG. 1. The processor 12 detects two or more markers from the data. A plurality of possible markers is each separately detected. Various locations are analyzed to determine whether there is a possible marker at the location. A machine-trained classifier performs the analysis. Multiple machine-trained classifiers may be applied for individual marker detection, such as in a bootstrapping approach. Features associated with each location are input to the classifier. The classifier outputs a score, such as a binary or score with greater dynamic range, indicating whether a possible marker is detected.

The processor 12 detects markers jointly. Different combinations of the markers output by the individual marker detection are input for joint detection. For each combination, the local context of the group of markers is used to determine features. The processor applies a classifier, such as another machine-trained classifier, to identify the group of markers most likely to be the actual markers.

The processor 12 detects the markers in a single frame of data. The detection is performed, at least initially, without data from other frames.

The display 16 is a CRT, LCD, plasma, projector, printer, or other output device for showing an image. The display 16 displays an image of two or more markers, such as one or more of the images shown in FIGS. 3b-c or 5. A stent enhanced image with markers enhanced and/or highlighted may be displayed. An image of marker characteristics may be displayed, such as displaying a value representing the distance between markers. In other embodiments, the markers are not displayed, are displayed to indicate the location, or are merely displayed as part of an image without highlighting or enhancement.

In one example embodiment, quantitative evaluation is conducted on a database of 1416 images from 36 different patients. Image resolutions may range from 0.13 to 0.19 mm/pixel. The images are normalized to be of 0.15 mm/pixel. The entire database may be randomly partitioned into two disjoint datasets, one for training and the other for independent testing. The training set contains 1214 image frames of 28 patient sequences. The independent test set is the remaining 182 frames of 8 patient sequences. Images from the same patient sequence are not used in both training and test sets. For each image frame, two balloon markers are manually annotated by human experts and used as the ground truth for evaluation. Other numbers of frames, sequences, resolutions, data divisions, or normalized levels may be used.

For each image, a pair of two balloon markers is detected in a fully automatic fashion using three PBT classifiers (two for individual detection with bootstrapping and one joint detector). Balloon markers may be automatically detected in fluoroscopic sequences. The learning strategy selects discriminative features from a large feature bank to distinguish the target markers from background. Context of both individual markers and joint marker pairs may be exploited. The data-driven method utilizes knowledge in the annotated database, providing a more robust solution in the presence of large image variations.

Euclidean distance is computed between the detected marker position and its ground truth counterpart as the detection error for each marker. The average error of the two markers is used as the metric to evaluate the system performance.

Table 1 shows the performance.

TABLE 1

| | Mean (pixels) | Std | Median (pixels) | Success rate (<3 pixels) | Stent enhancement success rate |
|---|---|---|---|---|---|
| Training | 6.4 | 38.7 | 1.1 | 97% | 100% |
| Independent evaluation set | 14.7 | 36.2 | 1.1 | 82% | 100% |

These results are obtained from single image frames without any assistance of temporal coherence. On average, it may take about 0.07 seconds to complete detection of both balloon markers in one frame, whose average dimensions are about 750×750. For each sequence, after applying temporal coherence analysis, registration, and averaging, the entire stent reconstruction and enhancement may be achieved in about 10 seconds. For 36 sequences, all the stents may be successfully enhanced. Balloon markers may be successfully detected in all the slices that were used for stent reconstruction and enhancement.

Stent enhancement success rate is defined as the approval rate by the human experts through visual inspection of the enhanced stent image using automatically detected markers. Large differences between mean and median values indicate the presence of outliers.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for marker detection in fluoroscopic imaging of a stent, the method comprising:
receiving, from a fluoroscopic scanner, a fluoroscopic scan of a patient;
masking the fluoroscopic scan of the patient to limit the number of locations to which marker detection is applied;
individually detecting a plurality of possible markers for a stent in one frame of fluoroscopic data from the fluoroscopic scan without information from other frames of fluoroscopic data from the fluoroscopic scan, the individual detecting being with a first machine-trained classifier, wherein the first machine-trained classifier does not detect masked out locations;
jointly detecting a pair of markers from the plurality of possible markers for the stent output from the individually detecting, the joint detecting being with a second machine-trained classifier, wherein the second machine-trained classifier does not detect masked out locations; and
outputting an image representing information about the pair of markers.

2. The method of claim 1 wherein individually detecting comprises detecting with the first machine-trained classifier comprising a probabilistic boosting tree classifier.

3. The method of claim 1 wherein individually detecting comprises detecting with first input features comprising Haar features and wherein jointly detecting comprises detecting with second input features comprising gradient features.

4. The method of claim 1 wherein individually detecting further comprises removing some of the possible markers with a third machine-trained classifier, the third machine-trained classifier operating on an output of the first machine-trained classifier and the second machine-trained classifier operating on an output of the third machine-trained classifier.

5. The method of claim 1 wherein jointly detecting comprises fitting a rectangular box defining a region over the pair of markers and detecting as a function of an input feature set comprising a gradient magnitude, a gradient angle, or both relative to the rectangular box.

6. The method of claim 1 wherein jointly detecting comprises detecting with the second machine-trained classifier comprising a probabilistic boosting tree classifier.

7. The method of claim 1 wherein individually detecting comprises determining a first score for each of the possible markers, and wherein jointly detecting comprises determining a second score for each of paired combinations of the possible markers;
further comprising calculating a third score for each of the paired combinations, the third score being a function of the first and second scores associated with the possible markers in the paired combination, the pair of markers being the paired combination with a highest score.

8. The method of claim 1 further comprising:
steerably filtering the frame of fluoroscopic data such that guide wire regions are distinguished from background; and
wherein individually detecting comprises sampling locations along the guide wire regions.

9. The method of claim 1 further comprising:
repeating individual and joint detecting for a plurality of frames of fluoroscopic data;
aligning the frames of fluoroscopic data as a function of the respective pairs of markers; and
combining the aligned frames into a stent frame of data; and
wherein outputting the image comprises outputting the image as a function of the stent frame of data.

10. The method of claim 1 wherein outputting the image comprises outputting an image comprising a fluoroscopic image with the pair of markers highlighted.

11. The method of claim 1 further comprising:
selecting a marker reference frame of data from a plurality of frames of fluoroscopic data, including the frame of fluoroscopic data, the selecting being as a function of a distance between markers in the pair of markers for each of the plurality of the frames and as a function of probabilities of the pair of markers being correct.

* * * * *